(12) United States Patent
Ehrhardt et al.

(10) Patent No.: US 10,151,915 B2
(45) Date of Patent: Dec. 11, 2018

(54) ILLUMINATION ARRANGEMENT, BEAM COMBINATION DEVICE AND METHOD FOR COUPLING AT LEAST THREE INPUT LIGHT BEAMS INTO AN OPTICAL WAVEGUIDE

(71) Applicants: KARL STORZ GmbH & Co. KG, Tuttlingen (DE); GRINTECH GmbH, Jena (DE)

(72) Inventors: André Ehrhardt, Wurmlingen (DE); Werner Goebel, Tuttlingen (DE); Bernhard Messerschmidt, Jena (DE)

(73) Assignees: KARL STORZ SE & Co. KG, Tuttlingen (DE); GRINTECH GmbH, Jena (DE)

( * ) Notice: Subject to any disclaimer, the term of this patent is extended or adjusted under 35 U.S.C. 154(b) by 219 days.

(21) Appl. No.: 15/275,692

(22) Filed: Sep. 26, 2016

(65) Prior Publication Data
US 2017/0090180 A1    Mar. 30, 2017

(30) Foreign Application Priority Data
Sep. 24, 2015   (DE) ........................ 10 2015 116 187

(51) Int. Cl.
*G02B 6/00*   (2006.01)
*G02B 23/24*  (2006.01)
(Continued)

(52) U.S. Cl.
CPC ............ *G02B 23/2469* (2013.01); *A61B 1/06* (2013.01); *G02B 3/0087* (2013.01);
(Continued)

(58) Field of Classification Search
None
See application file for complete search history.

(56) References Cited

U.S. PATENT DOCUMENTS 5,159,190 A    10/1992   Hohberg et al.
5,689,367 A    11/1997   Pan et al.
(Continued)

FOREIGN PATENT DOCUMENTS

DE              40 33 187 A1     4/1992
DE       10 2013 105 137 A1    11/2014
(Continued)

*Primary Examiner* — Tina M Wong
(74) *Attorney, Agent, or Firm* — Muncy, Geissler, Olds & Lowe, P.C.

(57) ABSTRACT

An illumination arrangement according to the invention, in particular for an endoscope, comprises at least three light sources for generating a respective input light beam, and a beam combination device (5, 21), wherein the beam combination device (5, 21) comprises at least two beam splitters for combining the at least three input light beams to form an output light beam, at least three collimator lenses (7, 8, 9) embodied as GRIN lenses and serving for collimating and coupling a respective one of the input light beams into one of the beam splitters, and at least one further GRIN lens for coupling the output light beam into an optical waveguide. The invention also relates to a beam combination device and a method for coupling at least three input light beams into an optical waveguide, in particular into an optical waveguide of an endoscope.

13 Claims, 2 Drawing Sheets

(51) Int. Cl.
  *A61B 1/06* (2006.01)
  *G02B 3/00* (2006.01)
  *F21V 8/00* (2006.01)
  *G02B 27/14* (2006.01)
  *G02B 27/28* (2006.01)
  *G02B 27/30* (2006.01)

(52) U.S. Cl.
  CPC ......... *G02B 6/0006* (2013.01); *G02B 27/141* (2013.01); *G02B 27/149* (2013.01); *G02B 27/283* (2013.01); *G02B 27/30* (2013.01)

(56) References Cited

U.S. PATENT DOCUMENTS

| | | | |
|---|---|---|---|
| 6,485,414 B1 | 11/2002 | Neuberger | |
| 8,885,033 B2 | 11/2014 | Masaki et al. | |
| 2002/0101634 A1 | 8/2002 | Ye | |
| 2006/0018214 A1* | 1/2006 | Fujii | G11B 7/082 369/44.37 |
| 2007/0183295 A1* | 8/2007 | Nagashima | G11B 7/1275 369/112.07 |
| 2007/0211604 A1* | 9/2007 | Ikenaka | G11B 7/1275 369/112.23 |
| 2007/0217316 A1* | 9/2007 | Ota | G11B 7/1374 369/112.23 |
| 2007/0230312 A1* | 10/2007 | Ikenaka | G02B 3/08 369/112.26 |
| 2008/0266526 A1* | 10/2008 | Kodama | G02B 27/283 353/20 |
| 2009/0097380 A1* | 4/2009 | Mizuno | G11B 7/1275 369/112.03 |
| 2009/0207716 A1* | 8/2009 | Tateyama | G11B 7/1275 369/112.24 |
| 2009/0252186 A1* | 10/2009 | Pan | H04N 9/3129 372/26 |
| 2010/0027402 A1* | 2/2010 | Iwata | G11B 7/1275 369/109.01 |
| 2010/0128592 A1* | 5/2010 | Kimura | G02B 3/08 369/112.23 |
| 2012/0268719 A1* | 10/2012 | Yamaguchi | G02B 27/283 353/20 |
| 2014/0340760 A1 | 11/2014 | Baumann et al. | |
| 2015/0316781 A1* | 11/2015 | Maeda | G02B 27/283 353/20 |
| 2015/0318951 A1* | 11/2015 | Zhang | G02B 27/28 398/65 |
| 2016/0328840 A1* | 11/2016 | Kiss | H04N 5/374 |
| 2017/0332056 A1* | 11/2017 | Ando | H04N 9/31 |
| 2018/0084982 A1* | 3/2018 | Yamashita | A61B 1/07 |

FOREIGN PATENT DOCUMENTS

| | | |
|---|---|---|
| GB | 2 076 994 A | 12/1981 |
| WO | WO 2010/127694 A1 | 11/2010 |

* cited by examiner

ILLUMINATION ARRANGEMENT, BEAM COMBINATION DEVICE AND METHOD FOR COUPLING AT LEAST THREE INPUT LIGHT BEAMS INTO AN OPTICAL WAVEGUIDE

This nonprovisional application claims priority under 35 U.S.C. § 119(a) to German Patent Application No. 10 2015 116 187.7, which was filed in Germany on Sep. 24, 2015, and which is herein incorporated by reference.

BACKGROUND OF THE INVENTION

Field of the Invention

The present invention relates to an illumination arrangement, in particular an illumination arrangement for an endoscope, a beam combination device and a method for coupling at least three input light beams into an optical waveguide, in particular into an optical waveguide of an endoscope.

Description of the Background Art

Endoscopic examination techniques have gained acceptance in a multiplicity of fields of application appertaining to medicine and animal medicine, but also in specific technical fields of application. In this case, an endoscope having an elongated shank with an imaging optical system is inserted into a cavity in order there to record an image of an object field and to transmit it to somewhere outside the body and thus to provide it for viewing and/or evaluation. The shank can be embodied such that it is rigid, semi-rigid or flexible. In order to illuminate the object field, the illumination light generated in the proximal region of the endoscope is usually guided to the distal end of the shank of the endoscope with the aid of optical fibers. Since the permissible external diameter of the shank of the endoscope is narrowly limited in many applications, the use of optical fibers having the smallest possible external diameter is advantageous.

For the endoscopic illumination, the illumination light generated by a light source is coupled into the optical fibers. Precisely in the case of very thin endoscopes it is desirable to use very thin optical fibers having a thickness of just a few 100 μm; in addition, said optical fibers have a high degree of flexibility, and so such illumination fibers can also be used in flexible endoscopes. However, conventional lamp systems such as xenon lamps or LEDs, for example, can be coupled into individual optical fibers having diameters of a few 100 μm only with high losses of illumination intensity. In principle, laser diodes make it possible to generate sufficiently bright illumination light which can even be coupled into very thin optical fibers with relatively low losses. Since laser diodes generate monochromatic light, for the endoscopic observation it is necessary to use a plurality of laser diodes which each generate light having a different wavelength. In particular, a combination of the three fundamental colors red, green and blue affords the possibility of generating white light. However, this necessitates a combination of the red, green and blue laser diode radiation generated by the respective laser diodes and coupling into a thin optical fiber.

Conventional RGB laser systems typically achieve a combination of the radiation of the red, green and blue laser diodes by virtue of the fact that the latter are fiber-coupled and the fibers of the individual laser diodes are combined in a common ferrule. This is followed by a further optical fiber encompassing the combined cross section of the three optical fibers of the laser diodes. As a result, this optical fiber that forwards the combined red-green-blue laser radiation necessarily has a larger diameter than the individual fibers connected to the respective laser diodes; such a combination is therefore unsuitable for particularly thin optical fibers. A combination of the red-green-blue laser diode radiation in a thin fiber can be achieved, in principle, by means of dichroic mirrors and lens systems. However, such arrangements have a high degree of adjustment sensitivity.

WO 2010/127694 A1 discloses an optical microprojection system in which three laser light sources for generating red, green and blue light and a beam combination device are provided for colored projection. The beam combination device is composed of optical components having coatings for wavelength-dependent reflection and transmission. The three laser light sources each have a collimator lens. The output beam, constituting a superimposition of the three light sources, is directed to the projection surface via a beam splitter cube, two quarter-wave plates and two movable micromirrors. A beam combination for coupling into an optical fiber is not provided.

In accordance with US 2002/0101634 A1 it is known that in a polarization beam combination device (Polarization Beam Combiner, PBC) used in optical communications technology, a plurality of dielectric layers on a diagonal surface between two prisms are used to combine with one another two beams that are incident at right angles to one another. A birefringent crystal can be used to combine two orthogonally polarized beams. US 2002/0101634 A1 proposes arranging a birefringent crystal having a surface inclined by approximately 3° to 30° between two GRIN lenses. Two entering beams, the polarization directions of which are directed in accordance with the axes of the birefringent crystal, are collimated by a GRIN lens and combined by the birefringent crystal into a single beam that is collimated by the second GRIN lens and coupled into an output fiber. The combination of more than two beams is not possible in this case.

SUMMARY OF THE INVENTION

It is an object of the present invention to provide an illumination arrangement, in particular an illumination arrangement for an endoscope, with which illumination light having a high brightness can be generated and coupled into an optical waveguide having a small diameter with the fewest possible losses. Furthermore, it is an object of the present invention to specify a beam combination device suitable therefor and a corresponding method for coupling at least three input light beams into an optical waveguide, in particular into an optical waveguide of an endoscope.

These objects are achieved by means of an illumination arrangement according to claim 1, a beam combination device according to claim 10 and a method according to claim 11. Advantageous developments of the invention are evident from the dependent claims.

An illumination arrangement according to the invention is preferably embodied as an illumination arrangement for an endoscope, i.e. for use in or with an endoscope for illuminating an object field in the case of an endoscopic observation. The illumination arrangement can be accommodated for example in the proximal end region of the endoscope or be embodied for instance as a separate light source unit that can be connected to a light connection of the endoscope via a light cable.

The illumination arrangement according to the invention comprises at least three light sources designed for generating a respective input light beam; overall, therefore, at least three input light beams can be generated. In the context of the present invention, "light" is understood to mean, in particular, visible light, but also radiation in the ultraviolet or infrared spectral range adjacent to the visible range.

The illumination arrangement according to the invention furthermore comprises a beam combination device for combining the at least three input light beams and for coupling into an optical waveguide. For this purpose, the beam combination device comprises at least two beam splitters which are designed and arranged for combining the at least three input light beams; the input light beams combined with one another form an output light beam. The customary designation "beam splitter" is used hereinafter, even if here the beam splitters serve for combining light beams. The beam splitters each have at least one beam-splitting splitter surface arranged in such a way that at least two input light beams impinge on substantially the same region of the splitter surface from different directions, wherein at least one of said input light beams is at least partly transmitted and at least one of said input light beams is at least partly reflected at the splitter surface in the same direction as the transmitted beam, such that both beams coincide after passing through the splitter surface and form a common beam. In this case, a first beam splitter can combine a first and a second input light beam to form an intermediate light beam, and a second beam splitter can be arranged in such a way that the intermediate light beam and a third input light beam are combined to form the output light beam.

Furthermore, the beam combination device of the illumination arrangement comprises at least three collimator lenses which are designed and arranged in each case for collimating an input light beam and for coupling the respective input light beam into one of the at least three beam splitters, for example for coupling the first and second input light beams into the first beam splitter and the third input light beam into the second beam splitter. The input light beams may have in each case a divergent beam path before passing through the assigned collimator lens and a substantially parallel beam path after passing through the collimator lens, in particular within the beam splitters. According to the invention, the collimator lenses are in each case embodied as gradient-index (GRIN) lenses and can include a plurality of lens elements cemented to one another, at least one of which consists of gradient-index material.

Furthermore, the beam combination device comprises a further lens, arranged and designed for coupling the output light beam into an optical waveguide; said further lens is likewise embodied as a GRIN lens according to the invention. Said further GRIN lens can also include a plurality of lens elements cemented to one another, at least one of which is formed of gradient-index material. In particular, the further GRIN lens is arranged in the beam path of the illumination arrangement downstream of the exit of the output light beam from the last beam splitter in the beam direction and acts as a converging lens for focusing the output light beam onto an end face of the optical waveguide. The optical waveguide can comprise at least one optical fiber, wherein the end face of the optical waveguide or of the at least one optical fiber can be arranged in such a way that the output light beam is focused onto the end face and enters the at least one optical fiber without relatively high losses. The illumination arrangement can comprise a mount for correspondingly positioning and fixing the optical waveguide or the at least one optical fiber. The optical waveguide or the at least one optical fiber can also be part of the illumination arrangement, wherein the end face is arranged and fixed in a corresponding manner.

If the illumination arrangement is accommodated in the proximal end region of an endoscope, the optical waveguide or the at least one optical fiber runs through the shank of the endoscope as far as the distal end thereof. If the illumination arrangement is embodied as a separate light source unit, the optical waveguide can run within the light cable that can be connected to a light connection of the endoscope.

The fact that at least two beam splitters are provided makes it possible according to the invention to combine three or more input light beams, which enable illumination of high light intensity, into an output light beam. By virtue of the fact that a respective GRIN lens is provided for collimating the input light beams and at least one further GRIN lens is provided for coupling the output light beam into the optical waveguide, a simple and compact configuration of the device is made possible since GRIN lenses are particularly simple to handle and to mount. Furthermore, the adjustment of the illumination arrangement is simplified.

In accordance with one preferred embodiment of the invention, the at least three light sources are designed for generating light in respectively different wavelength ranges. The different wavelength ranges can be substantially separated from one another; in particular, the light generated by the light sources can be in each case narrowband or even monochromatic. The illumination arrangement comprises, in particular, exactly three light sources that generate three input light beams in a total of three wavelength ranges, but can also comprise further light sources that generate light in one of said three wavelength ranges or else in one or more further wavelength ranges.

Furthermore, preferably at least one of the beam splitters, particularly preferably two beam splitters or all of the beam splitters, has a dichroic beam splitter layer adapted in each case to the wavelength ranges of the input light beams entering the respective beam splitter. For this purpose, in particular, the wavelength-dependent reflectance and the wavelength-dependent transmittance of the dichroic beam splitter layer are chosen in such a way that the input light beams entering the beam splitter can be combined with one another with the fewest possible losses. If a plurality of beam splitters have a dichroic beam splitter layer, the latter are preferably embodied differently and adapted to the wavelength ranges of the input light beams entering the respective beam splitter. The reflectance and the transmittance of the beam splitter layer can also depend on the angle of incidence at which an input light beam impinges on the beam splitter layer, and also on the degree of polarization and the polarization direction of the respective input light beam. The wavelength-dependent properties of the beam splitter layer are thus adapted to the wavelength ranges of the input light beams in such a way that light in the wavelength range of one input light beam is largely or completely reflected and light in the wavelength range of another input light beam is largely or completely transmitted, wherein the beam splitter layer can be optimized for the angles of incidence respectively present.

In this regard, for example, a first beam splitter can be arranged in such a way that a first and a second input light beam which enter the first beam splitter at right angles to one another impinge on a dichroic beam splitter layer of the first beam splitter in each case at an angle of approximately 45°. In this case, the first input light beam is transmitted and the second input light beam is reflected at the beam splitter layer in the same direction as the transmitted beam, such that the first and second input light beams coincide; the combined light beam that arises as a result is also designated here as "intermediate light beam". In this case, the dichroic beam splitter layer of the first beam splitter is advantageously designed for a high transmittance in the wavelength range of the first input light beam and for a high reflectance in the wavelength range of the second input light beam at an angle of incidence of 45°. If a second beam splitter is provided for combining the intermediate light beam and a third input light beam into the output light beam, then said second beam splitter can have a dichroic beam splitter layer that is correspondingly adapted to the wavelength range of the intermediate light beam, which comprises the wavelength ranges of the first and second input light beams, and to the wavelength range of the third input light beam. In this regard, the beam splitter layer can have for instance a high transmittance in the wavelength ranges of the intermediate light beam and a high reflectance in the wavelength range of the third input light beam, wherein the corresponding angles of incidence can likewise be taken into account. The intermediate light beam is thus predominantly or completely transmitted, and the third input light beam is predominantly or completely reflected, such that both are combined to form an output light beam comprising the first, the second and the third input light beams.

By virtue of the fact that at least three light sources are provided for generating input light beams with a total of at least three different wavelength ranges, and by virtue of the fact that at least one beam splitter, preferably all of the beam splitters, has a dichroic beam splitter layer adapted to the wavelength ranges of the input light beams entering the respective beam splitter, a low-loss combination of the input light beams is made possible. This enables an illumination of particularly high light intensity in a plurality of wavelength ranges which can cover a wide spectral range. In addition, the heat loss arising within the illumination arrangement can be reduced, which facilitates handling and enables a miniaturized embodiment.

However, it is preferred for the wavelength ranges of the at least three input light beams to complement one another at least approximately to form white light. In the context of the present application, the term "white light" is used for a spectral light composition that is perceived approximately as white. Such a light composition can have a continuous spectrum, but can also be generated for instance by combination of three narrowband or monochromatic primary colors. Preferably, the illumination arrangement has three light sources, of which a first generates red light, another generates green light and a further generates blue light. Such RGB light sources make it possible, in a simple manner, to generate illumination light which is perceived as white light and affords a multiplicity of application possibilities. In particular, the at least three light sources can be embodied or drivable in such a way that the input light beams generated by them, taking account of the entire transmission of the beam combination device, said transmission possibly being different for each of the at least three light sources, complement one another to form white light.

In accordance with one preferred embodiment of the invention, the light sources are embodied as laser light sources, in particular as laser diodes. The generation of light with a high intensity and a narrowband energy distribution is thereby made possible in a simple and cost-effective manner. The input light beams generated by the laser diodes can be particularly efficiently collimated, combined and coupled into the end face of the optical waveguide. It is particularly advantageous that a focusing of the output light beam onto a particularly small area is possible, and thus so is coupling even into a thin-lumen optical waveguide or an individual optical fiber having a core diameter of, for example, between 30 μm and 2 mm.

It is particularly preferred for the illumination arrangement to have as light sources three laser diodes, of which one generates red light, another generates green light and a further generates blue light. This makes possible, in a simple manner, a particularly bright illumination with light which is perceived as white light and affords a multiplicity of application possibilities.

In accordance with one preferred embodiment of the invention, at least one first and one second light source are designed for generating linearly polarized light, such that the first and second input light beams generated by these light sources are linearly polarized, preferably almost completely linearly polarized. Furthermore, in accordance with this embodiment, at least one of the beam splitters, namely one which the first and second input light beams enter, has a beam splitter layer adapted to the polarization directions of the first and second input light beams. In this case, the first and second input light beams have different polarization directions; in particular, the polarization directions can be perpendicular to one another. The beam splitter layer is embodied in particular in such a way that light having the polarization direction of one of the input light beams is predominantly reflected at the splitter surface and light having the polarization direction of the other input light beam is predominantly transmitted. A combination of the input light beams and thus an illumination of high light intensity with low losses can be made possible as a result. If at least the first and second light sources are embodied as laser light sources, in particular as laser diodes, the generation of the polarized input light beams is thereby made possible in a simple and cost-effective manner.

Particularly preferably, the first and second input light beams have different wavelength ranges and different polarization directions, the beam splitter layer of the beam splitter which the first and second input light beams enter is embodied as a dichroic beam splitter layer, and the wavelength-dependent transmission and reflection of the dichroic beam splitter layer are correspondingly chosen, taking account of the polarization of the first and second input light beams, to enable a combination of the input light beams with the fewest possible losses. With further preference, the first, the second and a third input light beam each have different wavelength ranges, and two beam splitters each have a dichroic beam splitter layer adapted to the wavelength ranges of the respective input light beams, of which the beam splitter layer of at least one beam splitter is simultaneously adapted to the polarization directions of the input light beams which enter said beam splitter. The respective beam splitter layer is in particular also optimized for the angles of incidence of the respective input light beams. In accordance with this aspect of the invention it has been recognized that a dichroic beam splitter layer, in particular a dichroic beam splitter layer embedded in glass, can be optimized only for one polarization direction, and that a particularly low-loss combination of the input light beams is therefore achievable if the input light beams are linearly polarized in different directions and these polarization directions are taken into account in the configuration of the beam splitter layer. A further improved illumination of high light intensity and also a further reduction of the heat loss are thereby made possible.

Preferably, at least one of the collimator lenses has a plane exit surface and is cemented to one of the beam splitters in such a way that the plane exit surface is cemented onto a likewise plane entrance surface of a beam splitter. The at least one collimator lens can also be cemented to the beam via an interposed glass rod. This makes use of the fact that GRIN lenses typically have plane entrance and exit surfaces and the collimator lens can thus be connected to the respective beam splitter in a particularly simple and secure manner and, in addition, in this case only interfaces between glass and cement occur and interfaces with air are avoided. Provision can also be made for a light source, for example a laser diode, or a holder of the light source, to be cemented to an entrance surface of the at least one collimator lens. In this way, adjustment can be facilitated and a low-loss forwarding of the input light beam collimated by the at least one collimator lens and coupled into the beam splitter can be made possible.

Furthermore, it is preferred for the at least two beam splitters to be embodied in each case as beam splitter cubes which are cemented to one another directly or via a glass rod with plane-parallel entrance and exit surfaces. The at least three collimator lenses, which are embodied as GRIN lenses and each have a plane exit surface, can be cemented in each case onto a likewise plane entrance surface of an assigned beam splitter cube, possibly via an interposed glass rod. A particularly stable and easily adjustable arrangement can be provided as a result, wherein the number of interfaces between air and glass through which the input beams pass is reduced further.

In accordance with one further preferred embodiment, a first and a second of the at least two beam splitters of the beam combination device are embodied in such a way that they each have a prism, wherein the prisms each have at least one entrance surface and a splitter surface, which is preferably inclined relative to the entrance surfaces. In particular, the prisms are embodied in each case as right prisms having a base surface in the form of a right-angled, equilateral triangle. In this case, the splitter surfaces of the two prisms are cemented to two mutually opposite surfaces of a glass rod embodied as a parallelepiped, such that a beam splitter rod comprising two beam splitters is formed. In this embodiment, the two beam splitters can thus respectively be regarded as beam splitter cubes, each of which is composed of two prisms, one prism of which in each case is embodied integrally with the glass rod. As a result, the number of interfaces can be reduced further; in particular, what can be achieved is that the light path of the intermediate light beam generated by the combination of a first and a second light beam in a first beam splitter runs between the splitter surfaces within the glass rod and thus does not pass through an interface. In this configuration of the beam splitters, too, the at least three collimator lenses can advantageously be cemented by a respective plane exit surface onto a likewise plane entrance surface of an assigned beam splitter, which may be a surface of a prism or of the glass rod embodied as a parallelepiped, possibly via an interposed glass rod. A particularly stable and easily adjustable arrangement can be provided as a result, wherein the number of interfaces between air and glass through which the input beams pass is minimal.

Particularly preferably, the at least one further GRIN lens of the beam combination device, which serves for coupling the output light beam into the optical waveguide, has a plane entrance surface by which it is cemented onto an exit surface of a beam splitter, namely of the last beam splitter in the beam path. The exit surface can be, in particular, a surface of a beam splitter cube or of the beam splitter rod embodied as described above. Preferably, in this case, only interfaces between glass and cement are present and, in particular, no air interspaces and thus no air-glass transitions are present.

The light losses in the beam combination device and thus in the illumination arrangement can be reduced further as a result.

In accordance with one preferred embodiment of the invention, the beam combination device, i.e. at least the beam splitters and the GRIN lenses are mounted, for example adhesively bonded, on a preferably planar baseplate. In this case, a configuration of the beam splitters as a beam splitter cube or as a beam splitter rod and a parallelepipedal configuration of the GRIN lenses enable a particularly simple and secure fixing by adhesive bonding on the baseplate. Particularly preferably, the beam splitters and the GRIN lenses are cemented to one another in the manner described above. Preferably, the light sources are also mounted on the baseplate. The baseplate can carry further components, for instance a power connection for supplying the light sources. As a result, a compact and stable arrangement is provided which facilitates the use of the illumination arrangement for example as a light source unit for an endoscope.

A beam combination device according to the invention is designed for combining at least three input light beams to form an output light beam and for coupling the output light beam into an optical waveguide. For this purpose, the beam combination device comprises at least two beam splitters for combining the at least three input light beams to form an output light beam, at least three collimator lenses embodied as GRIN lenses and serving for collimating and coupling a respective one of the input light beams into one of the beam splitters, and at least one further GRIN lens for coupling the output light beam into the optical waveguide. The beam combination device is embodied in particular as described above and suitable for use in an illumination arrangement according to the invention.

In a method according to the invention for coupling at least three input light beams into an optical waveguide, in particular into an optical waveguide of an endoscope, the at least three input light beams are collimated by means of a respective collimator lens embodied as a GRIN lens and are coupled into a respective one of at least two beam splitters and are combined to form an output light beam by means of the at least two beam splitters, and the output light beam is coupled into the optical waveguide by means of at least one further GRIN lens. Preferably, in the method according to the invention, it is furthermore provided that the at least three input light beams are generated by at least three light sources. The method according to the invention is carried out, in particular, with a beam combination device embodied as described above or an illumination arrangement embodied as described above.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
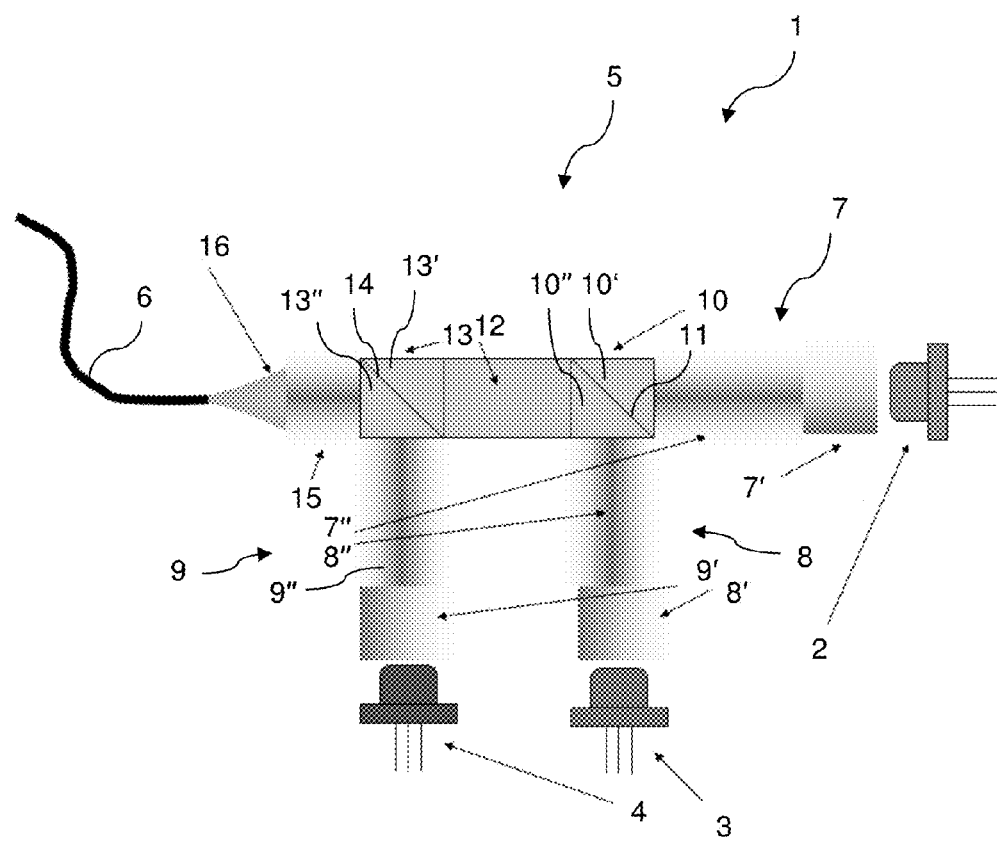
FIG. 1 shows an illumination arrangement in accordance with one exemplary embodiment of the invention in a schematic illustration.

As is illustrated schematically in FIG. 1, an illumination arrangement 1 in accordance with one exemplary embodiment of the invention comprises three laser diodes 2, 3, 4 and a beam combination device 5 for combining the input light beams generated by the three laser diodes 2, 3, 4 and for coupling the resultant output light beam into an optical waveguide, which comprises an optical fiber 6 in the example shown. The first laser diode 2 is designed for generating blue light, the second laser diode 3 is designed for generating red light, and the third laser diode 4 is designed for generating light in the green spectral range. The first input light beam generated by the first laser diode 2 and the second input light beam generated by the second laser diode 3 are perpendicular to one another and span a beam plane. The first input light beam is linearly polarized, wherein the polarization direction lies in the beam plane, i.e. in the plane of the drawing in FIG. 1. The second input light beam is polarized perpendicularly to the beam plane.

The generated first input light beam enters a first collimator lens 7, which has two lens elements respectively embodied as GRIN lenses, namely a cylindrical lens 7' and a converging lens 7". The cylindrical lens 7' serves for correcting the spatial emission characteristic of the laser diode 2 and the converging lens 7" serves for collimating the first input light beam, i.e. for generating a parallel beam of rays. Both the cylindrical lens 7' and the converging lens 7" each have planar axial entrance and exit surfaces and are cemented to one another at their end faces facing one another. In a corresponding manner, the second and third collimator lenses 8, 9 each having a cylindrical lens 8', 9' and a converging lens 8", 9", which are cemented to one another and collimate the second input light beam and third input light beam, respectively, which are generated by the second laser diode 3 and the third laser diode 4, respectively.

The first and second input light beams in each case as an approximately parallel beam of rays enter a first beam splitter cube 10 through respective entrance surfaces, said beam splitter cube having two prisms 10', 10", between which a dichroic beam splitter 11 is arranged. The first collimator lens 7 and the second collimator lens 8 are cemented in each case by their exit surface onto the entrance surfaces of the beam splitter cube 10. The first and second input light beams each impinge on the beam splitter layer 11 at an angle of approximately 45°. The wavelength- and polarization-dependent reflectance and transmittance of the beam splitter layer 11 are adapted to the wavelengths of the light generated by the first laser diode 2 and the second laser diode 3 taking account of the respective polarization directions in such a way that the transmittance is maximal in the blue spectral range for a linear polarization lying in the beam plane and that the reflectance is maximal in the red spectral range for a linear polarization directed perpendicular thereto. This makes it possible for the first and second input light beams to be combined to form a common light beam by the first beam splitter cube 10 with minimal losses. This light beam, which comprises the first and second input light beams and which is designated here as intermediate light beam, enters the plane-parallel glass rod 12, which is cemented to the beam splitter cube 10 at the opposite surface thereof relative to the entrance surface of the first input light beam.

On the opposite side of the glass rod 12 relative to the first beam splitter cube 10, said glass rod is cemented to the second beam splitter cube 13. The latter likewise has two prisms 13', 13", between which a dichroic beam splitter layer 14 inclined by approximately 45° is arranged. The third collimator lens 9 is cemented by its plane exit surface on a further entrance surface of the beam splitter cube 13. The third input light beam, which enters the second beam splitter cube 13 through the third collimator lens 9, is incident on the beam splitter layer 14 at an angle of approximately 45°. The spectral characteristic of the beam splitter layer 14 is likewise adapted to the wavelengths of the light generated by the laser diodes 2, 3, 4 and is chosen in such a way that the reflectance is maximal in the green spectral range, while the transmittance is maximal in the red and blue spectral ranges. As a result, the third input light beam is combined, largely without any losses, with the intermediate light beam to form an output light beam containing all three input light beams virtually unattenuated.

The output light beam enters a further lens embodied as a converging lens 15, which likewise is formed of GRIN material and which focuses the output light beam emerging from the second beam splitter cube 13 approximately as a parallel beam of rays onto the end face of the optical waveguide 6, said end face acting as an input surface. A further glass rod embodied as a glass cone 16 is arranged between the converging lens 15 and the optical fiber 6. The converging lens 5 has plane entrance and exit surfaces, in the same way as the glass cone 16, and is cemented to the latter and to the second beam splitter cube 13. The glass cone 16 serves to avoid interfaces between air and glass, and enables a low-loss coupling of the output light beam into the optical fiber 6. Within the beam combination device 5, the input light beams, the intermediate light beam and the output light beam do not pass through any air-glass interfaces.

The colors of the input light beams are indicated here merely by way of example. In this regard, for example, the first laser diode 2 can generate green light, the second laser diode 3 can generate blue light and the third laser diode 4 can generate red light, but other arrangements or wavelength ranges are also conceivable, which preferably complement one another to form white light. The wavelength-dependent properties of the beam splitter layers 11, 14 are correspondingly adapted for a low-loss combination of the input light beams.

Figure 2:
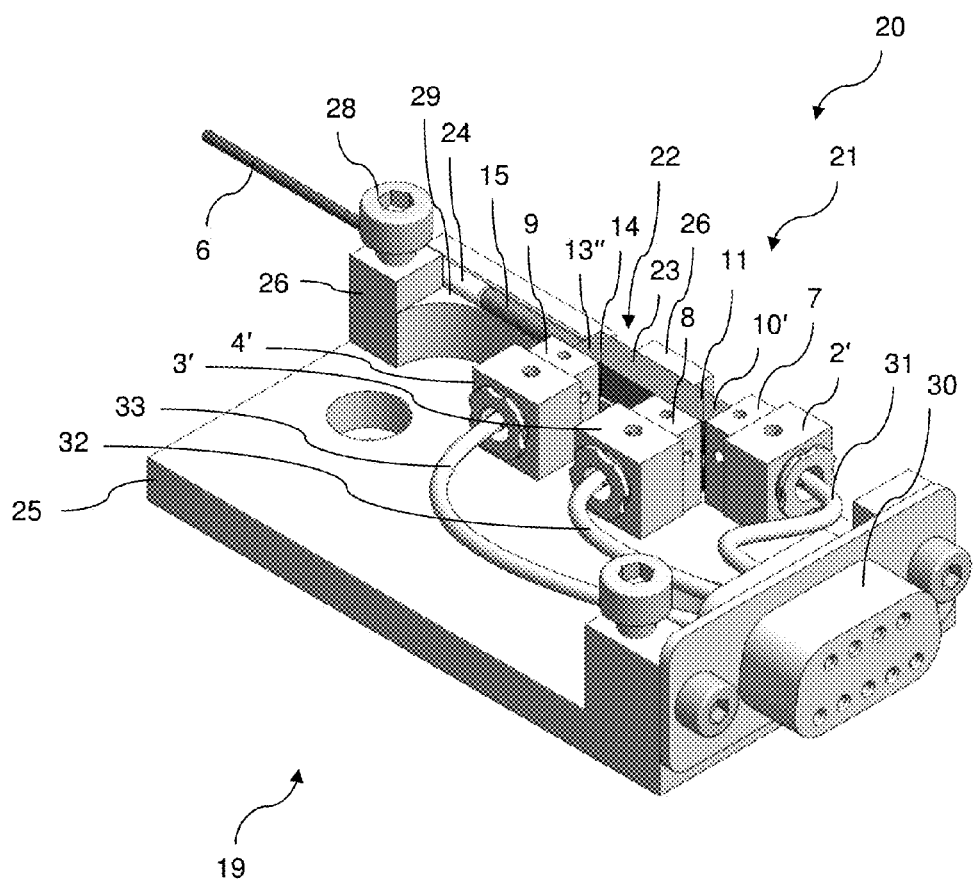
FIG. 2 shows an illumination unit comprising an illumination arrangement in accordance with a further exemplary embodiment of the invention in an oblique view.

FIG. 2 illustrates an illumination unit 19 comprising an illumination arrangement 20 embodied in accordance with a further exemplary embodiment of the invention.

Unless described otherwise, this illumination arrangement 20 is embodied like the exemplary embodiment described above. The illumination arrangement 20 comprises three laser diodes, which are held respectively in a holder 2', 3', 4' and which, as explained with regard to FIG. 1, generate blue, red and green light, respectively, wherein the first input light beam generated by the laser diode accommodated in the first holder 2' and the second input light beam generated by the laser diode accommodated in the second holder 3' are linearly polarized orthogonally with respect to one another. The input light beams are collimated by means of the respectively assigned collimator lens 7, 8, 9 embodied as a GRIN lens and are coupled into a beam splitter rod 22.

The beam splitter rod 22 comprises a glass rod 23 embodied as a parallelepiped and having an upper surface, a lower surface and two side surfaces, wherein the upper and lower surfaces adjoin the side surfaces in each case at right angles, and also two oblique surfaces, the normals to which in each case form an angle of approximately 45° and 135°, respectively, with the normals to the side surfaces. The glass rod 23 thus has the shape of a rectangular or square column whose end faces are inclined in each case by approximately 45°. The beam splitter rod 22 furthermore comprises two prisms 10', 13", which are arranged, for example cemented, on the oblique surfaces of the glass rod 23, wherein a respective beam splitter layer 11, 14 is situated between the glass rod 23 and the prisms 10', 13". The beam splitter layer 11, 14 can be applied to the respective oblique surface of the glass rod 23 or else to the corresponding surface of the respective prism 10', 13". The beam splitter layers 11, 14 are embodied as described with regard to FIG. 1 and are adapted to the wavelengths and polarizations of the input light beams generated by the laser diodes in such a way that the input light beams are combined to form an output light beam with minimal losses.

The output light beam emerges from the beam splitter rod 22 through a surface of the prism 13" and is coupled into an end face of the optical fiber 6 by means of a converging lens 15, likewise embodied as a GRIN lens. A further glass rod interposed between the converging lens 15 and the optical fiber 6 can be omitted, depending on the design of the converging lens 15. An end section of the optical fiber 6 is mounted in a ferrule 24 and held in the illumination unit 19, such that the end face of the optical fiber 6 lies in the focal region of the converging lens 15.

The elements of the illumination arrangement 20 of the illumination unit 19 are fixed on a baseplate 25. In particular, the collimator lenses 7, 8, 9 are embodied in a parallelepipedal fashion and are adhesively bonded onto the baseplate 25. The holders 2', 3', 4' of the laser diodes can likewise be embodied in a parallelepipedal fashion and be fixed on the baseplate 25 by adhesive bonding. In the example shown, the beam splitter rod 22 is also embodied overall in a parallelepipedal fashion and is fixed via a carrier 26 on the baseplate 25 by adhesive bonding and is cemented to the collimator lens 7, 8, 9 and the converging lens 15. On the baseplate 25, furthermore, a mount 27 for the optical fiber 6 is fixed, wherein the ferrule 24 is pressed against a bearing surface 29 for example by means of a clamping screw 28. The baseplate 25 also carries a connection socket 30 for supplying electrical energy to the laser diodes via the cables 31, 32, 33. The illumination arrangement illustrated in FIG. 1 can also be mounted on a baseplate in a corresponding manner.

In the exemplary embodiment illustrated in FIG. 2, by way of example, the collimator lenses 7, 8, 9 can have a length of approximately 3.3 mm measured in the beam direction, and the converging lens can have a length of approximately 10.6 mm, while the beam splitter rod can be embodied as a square column having edge lengths of 3 mm, 3 mm and 11 mm. In this way, a coupling of the illumination light generated by the laser diodes into the optical fiber 6, which can have a core diameter of 100 μm, for example, with a numerical aperture of approximately 0.22, can be achieved with a compact arrangement.

For the sake of clarity, not all of the figures illustrate all of the reference signs. Reference signs not explained with regard to a figure have the same meaning as in the other figures.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. An illumination arrangement comprising:
    at least three light sources for generating a respective input light beam, and
    a beam combination device,
    wherein the beam combination device comprises:
        at least two beam splitters for combining the at least three input light beams to form an output light beam,
        at least three collimator lenses embodied as GRIN lenses and serving for collimating and coupling a respective one of the input light beams into one of the beam splitters, and
        at least one further GRIN lens for coupling the output light beam into an optical waveguide,
    wherein the at least one further GRIN lens has a plane entrance surface by which the at least one further GRIN lens is cemented directly onto an exit surface of one of the at least two beam splitters.

2. The illumination arrangement according to claim 1, wherein the at least three light sources are designed for generating the input light beams with respectively different wavelength ranges, and in that at least one of the beam splitters has a dichroic beam splitter layer adapted to the wavelength ranges of at least two input light beams.

3. The illumination arrangement according to claim 2, wherein the wavelength ranges of the input light beams complement one another at least approximately to form white light.

4. The illumination arrangement according to claim 1, wherein the at least three light sources are embodied as laser diodes.

5. The illumination arrangement according to claim 1, wherein at least two of the light sources are designed for generating at least two input light beams with different polarization directions, and in that at least one beam splitter which the at least two input light beams enter has a beam splitter layer adapted to the polarization directions of the at least two input light beams.

6. The illumination arrangement according to claim 1, wherein at least one first and one second light source are designed for generating a first and a second input light beam having different wavelength ranges and different polarization directions, and in that at least one beam splitter which the first and the second input light beams enter has a beam splitter layer adapted to the wavelength ranges and the polarization directions of the first and second input light beams.

7. The illumination arrangement according to claim 1, wherein at least one of the collimator lenses has a plane exit surface by which it is cemented onto an entrance surface of one of the beam splitters.

8. The illumination arrangement according to claim 7, wherein the at least two beam splitters are embodied as beam splitter cubes which are cemented to one another directly or via a glass rod, and in that the at least three collimator lenses in each case have a plane exit surface by which they are in each case cemented onto an entrance surface of a beam splitter cube.

9. The illumination arrangement according to claim 7, wherein two of the beam splitters each have a prism, wherein the two prisms each have at least one entrance surface and a splitter surface, and wherein the splitter surfaces of the two prisms are cemented to two mutually opposite surfaces of a glass rod embodied as a parallelepiped.

10. The illumination arrangement according to claim 1, characterized in that the at least two beam splitters, the at least three collimator lenses and the at least one further GRIN lens are mounted on a baseplate.

11. Beam A beam combination device for combining at least three input light beams and for coupling into an optical waveguide, comprising:
- at least two beam splitters for combining the at least three input light beams to form an output light beam,
- at least three collimator lenses embodied as GRIN lenses and serving for collimating and coupling a respective one of the input light beams into one of the beam splitters, and
- at least one further GRIN lens for coupling the output light beam into an optical waveguide,
- wherein the at least one further GRIN lens has a plane entrance surface by which the at least one further GRIN lens is cemented directly onto an exit surface of one of the at least two beam splitters.

12. A method for coupling at least three input light beams into an optical waveguide, wherein at least three input light beams are collimated by means of a respective collimator lens embodied as a GRIN lens and are coupled into a respective one of at least two beam splitters and are combined to form an output light beam by means of the at least two beam splitters, and wherein the output light beam is coupled into the optical waveguide by means of at least one further GRIN lens, wherein the at least one further GRIN lens has a plane entrance surface by which the at least one further GRIN lens is cemented directly onto an exit surface of one of the at least two beam splitters.

13. The illumination arrangement according to claim 1, wherein the illumination arrangement is for an endoscope and wherein the optical waveguide is an optical fiber.

* * * * *